(12) United States Patent
Fujimoto et al.

(10) Patent No.: US 8,919,607 B2
(45) Date of Patent: Dec. 30, 2014

(54) ANALYTE TEST STRIP VIAL

(75) Inventors: Frank David Fujimoto, Fremont, CA (US); Craig W. Sharp, San Francisco, CA (US); Philip Justus Wunderle, III, El Cerrito, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 653 days.

(21) Appl. No.: 12/860,163

(22) Filed: Aug. 20, 2010

(65) Prior Publication Data
US 2011/0253736 A1 Oct. 20, 2011

Related U.S. Application Data

(60) Provisional application No. 61/325,012, filed on Apr. 16, 2010.

(51) Int. Cl.
*B65G 59/00* (2006.01)
*B65H 3/00* (2006.01)
*G07F 11/16* (2006.01)

(52) U.S. Cl.
USPC ........... 221/267; 267/309; 267/306; 267/310; 267/1; 267/199; 267/251; 433/61; 433/99; 433/104; 433/174; 433/183; 220/694; 220/281; 414/800; 206/204; 206/449; 429/52

(58) Field of Classification Search
CPC .......... B65G 59/00; B65H 3/00; G07F 11/16
USPC .............. 422/61, 99, 104, 174, 183; 221/199, 221/251, 267, 309, 306, 310, 1; 220/694, 220/281; 414/800; 206/204, 449; 429/52
See application file for complete search history.

(56) References Cited

U.S. PATENT DOCUMENTS

| | | | | |
|---|---|---|---|---|
| 1,846,068 A | * | 2/1932 | Sandehn | 239/39 |
| 2,094,961 A | * | 10/1937 | Quattrin | 215/14 |
| 2,918,167 A | * | 12/1959 | Lowen | 206/540 |
| 6,071,391 A | | 6/2000 | Gotoh et al. | |
| 6,143,164 A | | 11/2000 | Heller et al. | |
| 6,592,745 B1 | | 7/2003 | Feldman et al. | |
| 6,616,819 B1 | | 9/2003 | Liamos et al. | |
| 6,662,950 B1 | * | 12/2003 | Cleaver | 206/710 |
| 6,893,545 B2 | | 5/2005 | Gotoh et al. | |
| 7,628,292 B2 | * | 12/2009 | Lancesseur et al. | 221/267 |
| 7,810,673 B2 | * | 10/2010 | Lancesseur et al. | 221/265 |
| 7,887,757 B2 | * | 2/2011 | Chan | 422/500 |
| 8,066,957 B2 | * | 11/2011 | Chan et al. | 422/401 |
| 8,322,567 B2 | * | 12/2012 | Giraud | 220/839 |
| 2003/0185705 A1 | * | 10/2003 | Otake | 422/58 |
| 2003/0185708 A1 | * | 10/2003 | Otake | 422/61 |
| 2006/0025662 A1 | | 2/2006 | Buse et al. | |
| 2006/0091006 A1 | | 5/2006 | Wang et al. | |

(Continued)

*Primary Examiner* — Rakesh Kumar
(74) *Attorney, Agent, or Firm* — Edward J. Baba; Shweta H. Chandra; Bozicevic, Field & Francis LLP

(57) ABSTRACT

An analyte test strip vial having a restrictor to dispense analyte test strips in a controlled manner. In general, the restrictor includes one or more openings (e.g., central and/or arc-shaped openings) that are appropriately sized to facilitate the dispensing of a manageable number of analyte test strips from the vial container. The restrictor may also include one or more surface features (e.g., tabs, cavities, and/or tapered surfaces) to facilitate in the removal of analyte test strips, and the matting and/or removal of the restrictor from the vial container.

24 Claims, 17 Drawing Sheets

(56) References Cited

U.S. PATENT DOCUMENTS

| | | | |
|---|---|---|---|
| 2006/0169603 A1* | 8/2006 | Lancesseur et al. | 206/204 |
| 2007/0034630 A1* | 2/2007 | Lancesseur et al. | 220/281 |
| 2007/0068807 A1 | 3/2007 | Feldman et al. | |
| 2007/0095661 A1 | 5/2007 | Wang et al. | |
| 2007/0108048 A1 | 5/2007 | Wang et al. | |
| 2007/0199818 A1 | 8/2007 | Petyt et al. | |
| 2007/0264166 A1* | 11/2007 | West et al. | 422/104 |
| 2008/0060196 A1 | 3/2008 | Wang et al. | |
| 2008/0066305 A1 | 3/2008 | Wang et al. | |
| 2008/0102441 A1 | 5/2008 | Chen et al. | |
| 2008/0118400 A1* | 5/2008 | Neel et al. | 422/68.1 |
| 2008/0148873 A1 | 6/2008 | Wang | |
| 2008/0267823 A1 | 10/2008 | Wang et al. | |
| 2009/0095625 A1 | 4/2009 | Forrow | |
| 2009/0255811 A1 | 10/2009 | Forrow et al. | |
| 2010/0000905 A1* | 1/2010 | Wang et al. | 206/569 |
| 2010/0249652 A1* | 9/2010 | Rush et al. | 600/583 |
| 2010/0331771 A1* | 12/2010 | Mazza et al. | 604/66 |
| 2011/0168827 A1* | 7/2011 | Cooper | 242/160.4 |
| 2012/0080330 A1* | 4/2012 | Rush et al. | 206/305 |
| 2012/0148882 A1* | 6/2012 | Bakker | 429/52 |
| 2012/0199601 A1* | 8/2012 | Sawa | 221/1 |
| 2013/0017056 A1* | 1/2013 | Myles et al. | 414/800 |

\* cited by examiner

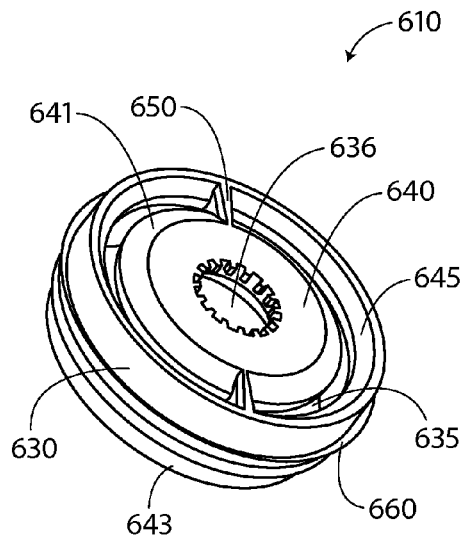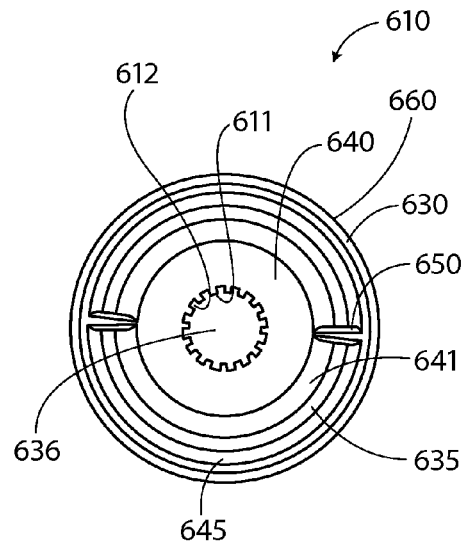
FIG. 6A  FIG. 6B
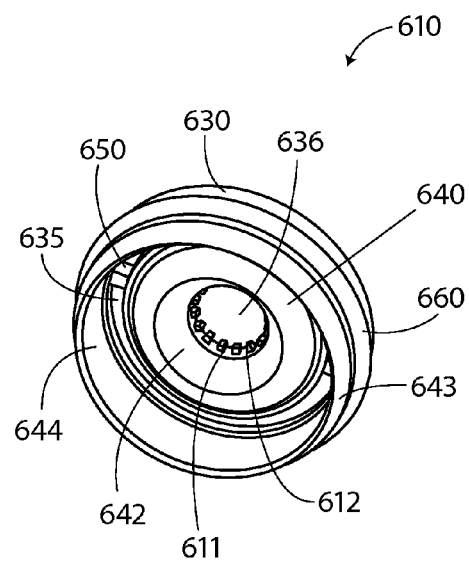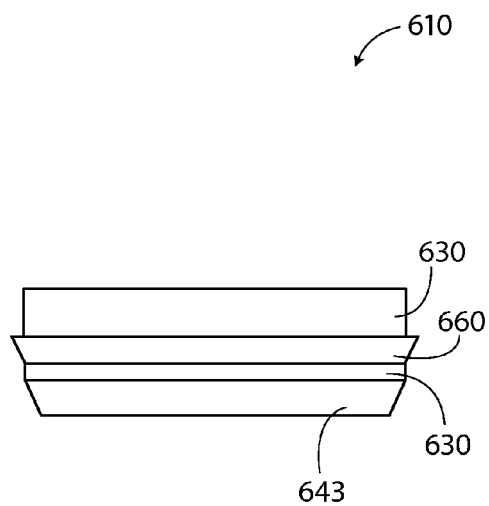
FIG. 6C  FIG. 6D

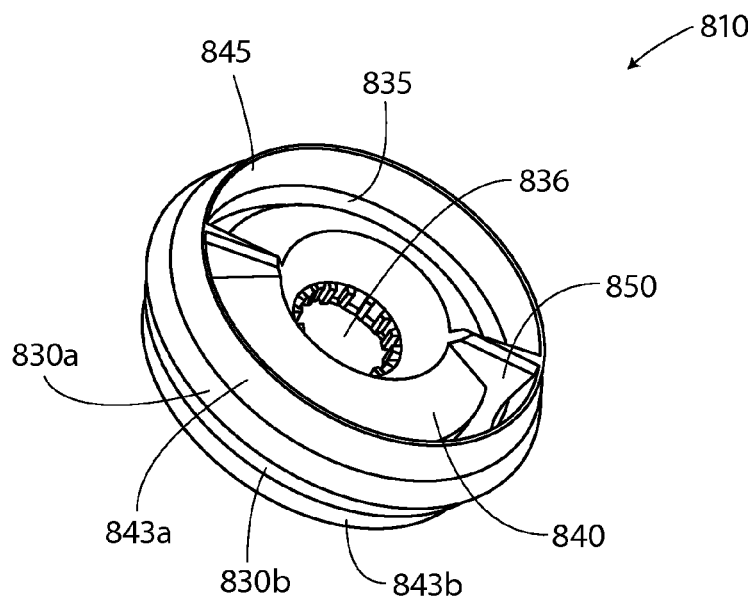
FIG. 8A
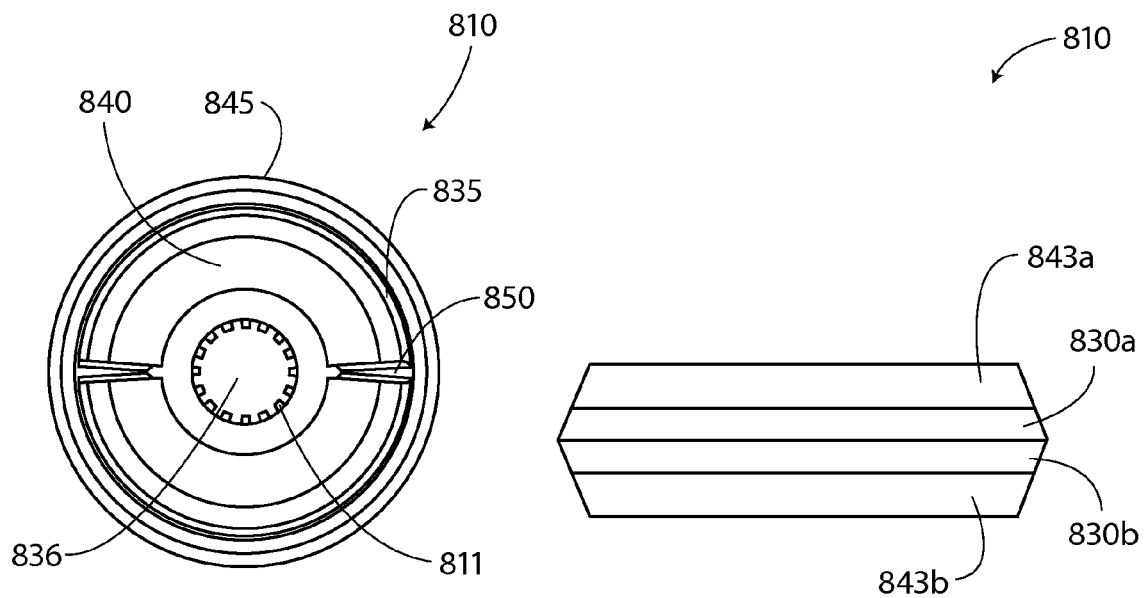
FIG. 8B  FIG. 8C

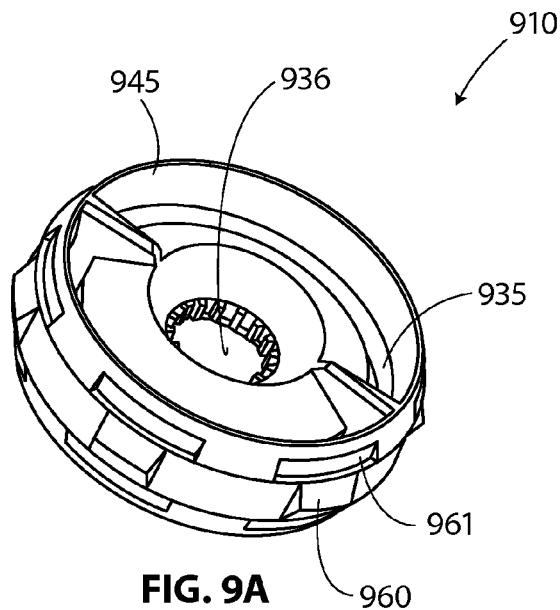
FIG. 9A
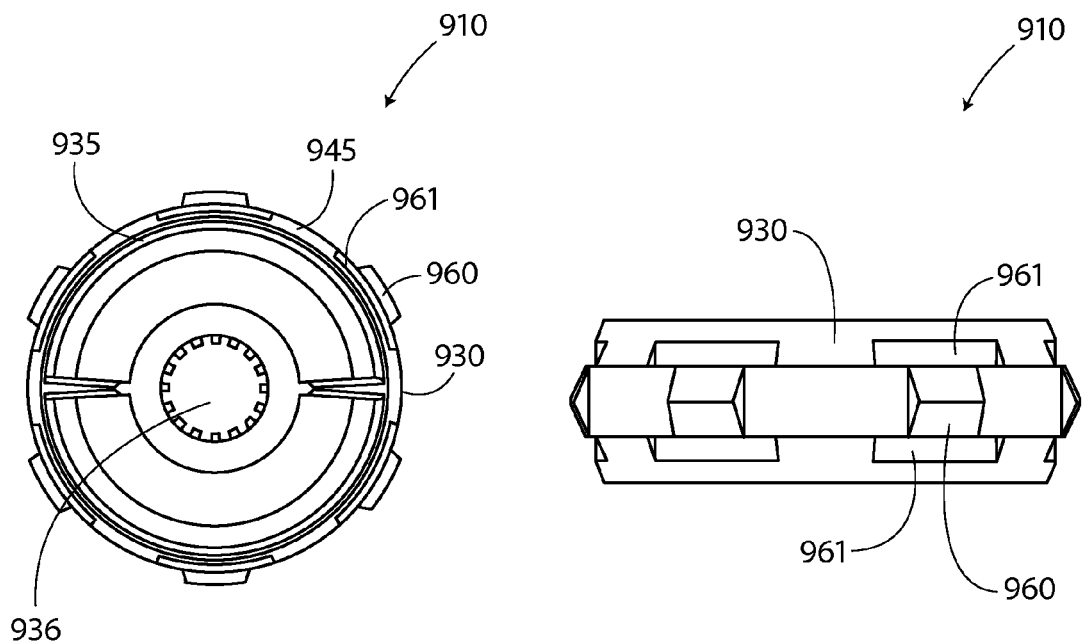
FIG. 9B  FIG. 9C

ANALYTE TEST STRIP VIAL

CROSS REFERENCE TO RELATED APPLICATIONS

This application claims priority based on U.S. Provisional Application No. 61/325,012, filed on Apr. 16, 2010, the disclosure of which is herein incorporated by reference in its entirety.

This application is related to commonly owned U.S. patent application Ser. No. 12/168,009 (Publication No. 2010/0000905), filed on Jul. 3, 2008, and Ser. No. 12/465,942, filed on May 14, 2009, which are herein incorporated by reference in their entirety.

BACKGROUND OF THE INVENTION

1. Field of the Invention

The present invention relates to a vial for storing a plurality of analyte test strips. More specifically, the present invention relates to a vial adapted to dispense analyte test strips in a controlled manner.

2. Background

Analyte test strips, such as those used by diabetics to test blood glucose levels, are typically distributed and stored in vials. Such vials are generally cylindrical containers with open ends closed by a cap. The inventors have found that users of standard vials experience difficulties in withdrawing a controlled number of test strips from within the container. Difficulties arise due to users' lack of dexterity and/or hand-eye coordination. For example, a problem arises when a user tilts the container to withdraw a single analyte test strip, but accidentally spills a much larger number of analyte test strips from the container.

For additional background information, reference is made to U.S. Patent Application Publication 2010/0000905.

BRIEF SUMMARY OF THE INVENTION

To overcome the disadvantages of conventional analyte test strip vials, the inventors have developed an insert (herein referred to as a "restrictor") to dispense analyte test strips in a controlled manner. Various embodiments and examples are provided. In general, a restrictor in accordance with the present invention includes one or more openings (e.g., central and/or arc-shaped openings) that are appropriately sized to facilitate the dispensing of a manageable number of analyte test strips from the vial container. The restrictor may also include one or more surface features (e.g., tabs, cavities, and/or tapered surfaces) to facilitate in the removal of analyte test strips, and the mating and/or removal of the restrictor from the vial container.

BRIEF DESCRIPTION OF THE FIGURES

The accompanying drawings, which are incorporated herein, form part of the specification. Together with this written description, the drawings further serve to explain the principles of, and to enable a person skilled in the relevant art(s), to make and use an analyte test strip vial in accordance with the present invention. In the drawings, with limited exception, like reference numbers indicate identical or functionally similar elements.

FIG. 6A is a front-side angled view of a restrictor in accordance with another embodiment presented herein.

FIG. 6B is a front-side view of the restrictor of FIG. 6A.

FIG. 6C is a back-side angled view of the restrictor of FIG. 6A.

FIG. 6D is a side view of the restrictor of FIG. 6A.

FIG. 8A is a front-side angled view of a restrictor in accordance with one embodiment presented herein.

FIG. 8B is a front-side view of the restrictor of FIG. 8A.

FIG. 8C is a side view of the restrictor of FIG. 8A.

FIG. 9A is a front-side angled view of a restrictor in accordance with one embodiment presented herein.

FIG. 9B is a front-side view of the restrictor of FIG. 9A.

FIG. 9C is a side view of the restrictor of FIG. 9A.

DETAILED DESCRIPTION OF THE INVENTION

Figure 1:
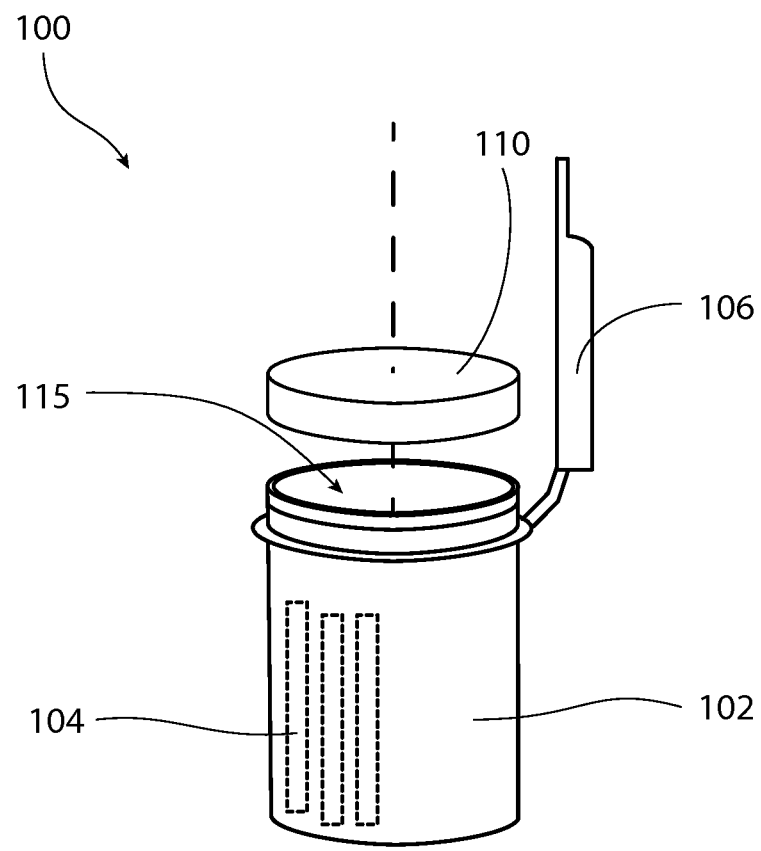
FIG. 1 is a schematic view illustrating the general nature of the present invention.

Before the embodiments of the present disclosure are described, it is to be understood that this invention is not limited to particular embodiments described, as such may, of course, vary. It is also to be understood that the terminology used herein is for the purpose of describing particular embodiments only, and is not intended to be limiting, since the scope of the embodiments of the invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

In the description of the invention herein, it will be understood that a word appearing in the singular encompasses its plural counterpart, and a word appearing in the plural encompasses its singular counterpart, unless implicitly or explicitly understood or stated otherwise. Merely by way of example, reference to "an" or "the" "analyte" encompasses a single analyte, as well as a combination and/or mixture of two or more different analytes, reference to "a" or "the" "concentration value" encompasses a single concentration value, as well as two or more concentration values, and the like, unless implicitly or explicitly understood or stated otherwise. Further, it will be understood that for any given component described herein, any of the possible candidates or alternatives listed for that component, may generally be used individually or in combination with one another, unless implicitly or explicitly understood or stated otherwise. Additionally, it will be understood that any list of such candidates or alternatives, is merely illustrative, not limiting, unless implicitly or explicitly understood or stated otherwise.

Various terms are described below to facilitate an understanding of the invention. It will be understood that a corresponding description of these various terms applies to corresponding linguistic or grammatical variations or forms of these various terms. It will also be understood that the invention is not limited to the terminology used herein, or the descriptions thereof, for the description of particular embodiments. Merely by way of example, the invention is not limited to particular analytes, bodily or tissue fluids, blood or capillary blood, or sensor constructs or usages, unless implicitly or explicitly understood or stated otherwise, as such may vary.

The publications discussed herein are provided solely for their disclosure prior to the filing date of the application. Nothing herein is to be construed as an admission that the embodiments of the invention are not entitled to antedate such publication by virtue of prior invention. Further, the dates of publication provided may be different from the actual publication dates which may need to be independently confirmed.

The following detailed description of the figures refers to the accompanying drawings that illustrate exemplary embodiments of an analyte test strip vial and associated restrictor. Other embodiments are possible. Modifications may be made to the embodiments described herein without departing from the spirit and scope of the present invention. Therefore, the following detailed description is not meant to be limiting.

FIG. 1 is a schematic view illustrating the general nature of the present invention. As shown in FIG. 1, the present invention provides a vial 100 having a plurality of analyte test strips 104 disposed therein. Analyte test strips 104 can be of any kind, size, or shape known to those skilled in the art; for example, FREESTYLE® and FREESTYLE LITE™ test strips sold by ABBOTT DIABETES CARE Inc. In one example, analyte test strips 104 are used to test glucose levels for diabetic patients. Vial 100 includes a cylindrical container 102 having an open end 115, and a cap 106 (or lid) to close the open end 115 of container 102. FIG. 1 illustrates a generic insert, or restrictor 110 (which may be replaced by any of the herein described restrictors, and equivalents thereof). As shown, restrictor 110 is inserted into the open end 115 of container 102.

In addition to the embodiments specifically disclosed herein, the vials of the present disclosure can be configured to work with a wide variety of analyte sensors, e.g., those disclosed in U.S. patent application Ser. No. 11/461,725, filed Aug. 1, 2006; U.S. Patent Application Publication No. 2007/0095661; U.S. Patent Application Publication No. 2006/0091006; U.S. Patent Application Publication No. 2006/0025662; U.S. Patent Application Publication No. 2008/0267823; U.S. Patent Application Publication No. 2007/0108048; U.S. Patent Application Publication No. 2008/0102441; U.S. Patent Application Publication No. 2008/0066305; U.S. Patent Application Publication No. 2007/0199818; U.S. Patent Application Publication No. 2008/0148873; U.S. Patent Application Publication No. 2007/0068807; U.S. patent application Ser. No. 12/102,374, filed Apr. 14, 2008, and U.S. Patent Application Publication No. 2009/0095625; U.S. Pat. No. 6,616,819; U.S. Pat. No. 6,143,164; U.S. Pat. No. 6,592,745; U.S. Pat. No. 6,071,391 and U.S. Pat. No. 6,893,545; the disclosures of each of which are incorporated by reference herein.

As will be fully explained below, container 102, and equivalents thereof, serve as means for storing analyte test strips. Cap 106, and equivalents thereof, serve as means for closing the container 102. The herein provided embodiments of restrictors, and equivalents thereof, serve as means for dispensing analyte test strips in a controlled manner. As used herein, to "dispense analyte test strips in a controlled manner" is intended to mean "withdrawing a manageable number of test strips, preferably but not limited to one test strip." For example, a "manageable number of test strips" may be 1-5 test strips when the container is holding 25 or more test strips.

Figure 2:
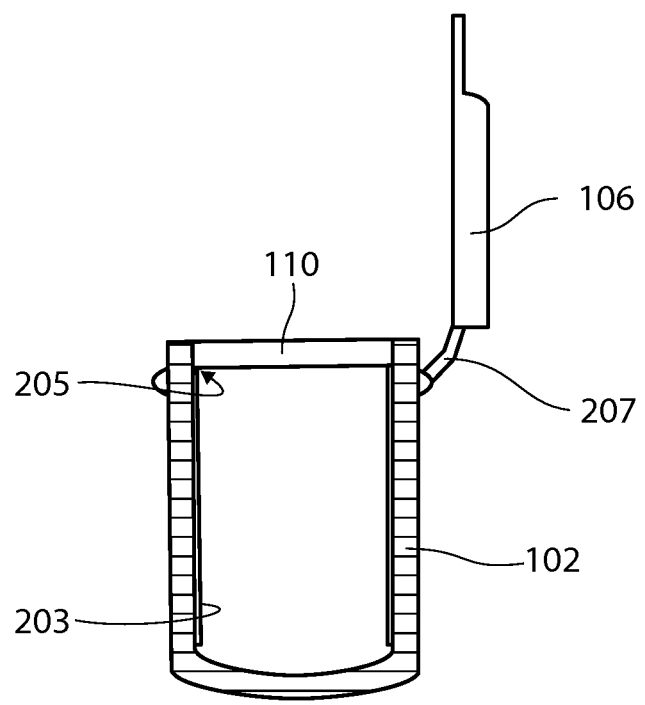
FIG. 2 is a cross-sectional view of the container depicted in FIG. 1.

FIG. 2 is a cross-sectional view of container 102. In the embodiment shown, container 102 includes an optional desiccant layer 203 bound or coated to an inner surface of container 102. Such desiccant layer 203 is provided to keep analyte test strips 104 relatively dry within container 102. Further, desiccant layer 203 and/or the inner surface structure of container 102 forms a shoulder region 205 for mating with restrictor 110. As used herein, the terms "mate" or "mating" are intended to mean: "to join, fit, connect, link, or associate suitably." In one embodiment, shoulder region 205 is designed such that restrictor 110 lies flush with the top surface of container 102. As used herein, the term "flush" is intended to mean: "on plane with, or aligned on plane with." In an alternative embodiment, restrictor 110 may be recessed within container 102, or may extend distal of the top surface of container 102. FIG. 2 further illustrates cap 106 in a hinged 207 configuration. As such, cap 106 is adapted to close the open end 115 of container 102. An optional desiccant layer 203, or equivalents thereof, serves as means for maintaining the analyte test strips dry.

Figure 3A:
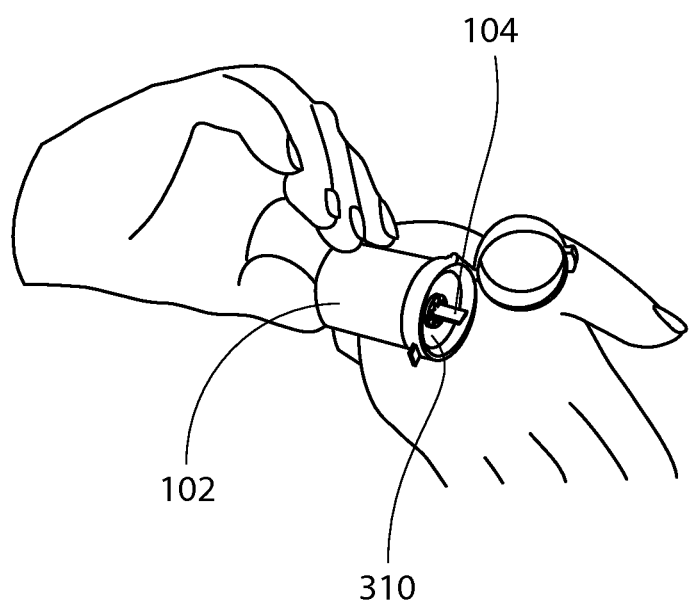
FIG. 3A is an illustration showing a user employing a restrictor, in accordance with one embodiment presented herein, to dispense an analyte test strip in a controlled manner.
Figure 3B:
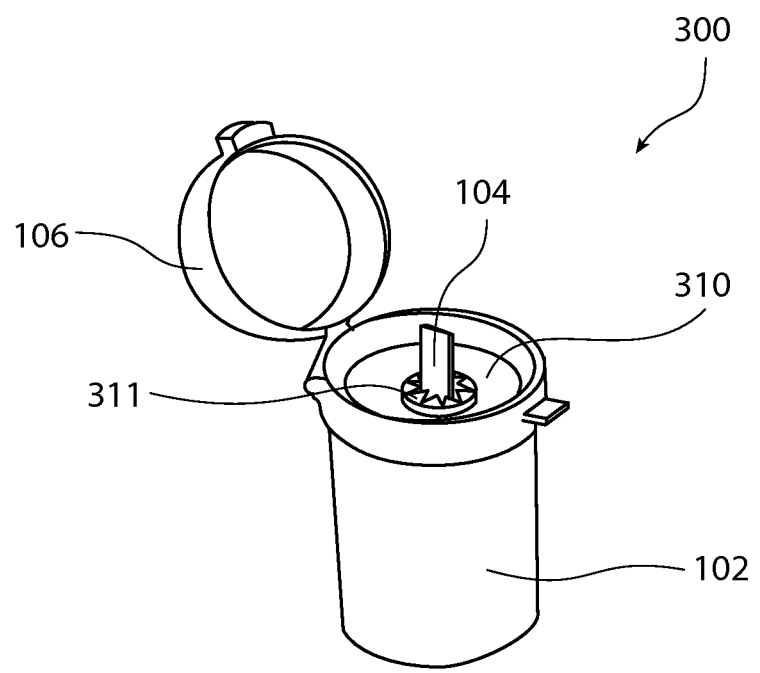
FIG. 3B is a perspective view of the embodiment depicted in FIG. 3A.

FIG. 3A shows a user employing a restrictor 310, in accordance with one embodiment presented herein, to dispense analyte test strips in a controlled manner. In use, a user tilts and/or shakes container 102 until an analyte test strip 104 is dispensed from an opening in restrictor 310. As such, the user avoids spilling an unwanted number of test strips for container 102. FIG. 3B is a perspective view of vial 300, with analyte test strip 104 partially withdrawn through restrictor 310. As shown, restrictor 310 includes a central opening defined by a saw-tooth edge 311. In one embodiment, saw-tooth edge 311 is configured (i.e., sized) such that only a one analyte test strip 104 can exit through the central opening at a time. For example, opposing points of saw-tooth edge 311 may be distanced between about 0.20 inches and about 0.30 inches from one another (such dimensions, as well as all dimensions mentioned herein, being based on standard analyte test strip dimensions). In another example, opposing points of saw-tooth edge 311 may be distanced between about 0.227 inches and about 0.233 inches from one another. Further, adjacent points of saw-tooth edge may be distanced between about 0.005 inches and about 0.030 inches from one another. In another example, adjacent points of saw-tooth edge may be distanced between about 0.002 inches and about 0.045 inches from one another. In one embodiment, sawtooth edge 311 is formed of a pliable rubber or polymer material, such as polyethylene terephthalate (PET), and the area surrounding saw-tooth edge 311 is formed of a hard plastic material.

Figure 3C:
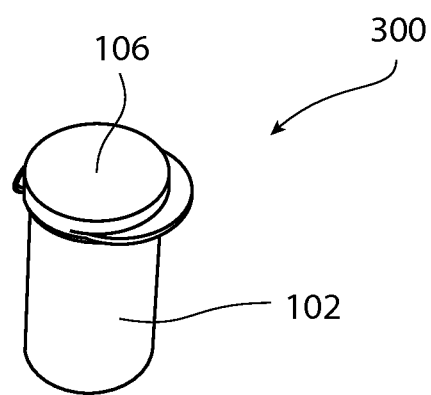
FIG. 3C is a perspective view illustrating a closed vial.

FIG. 3C is a perspective view illustrating vial 300 with cap 106 in a closed position.

Figure 4:
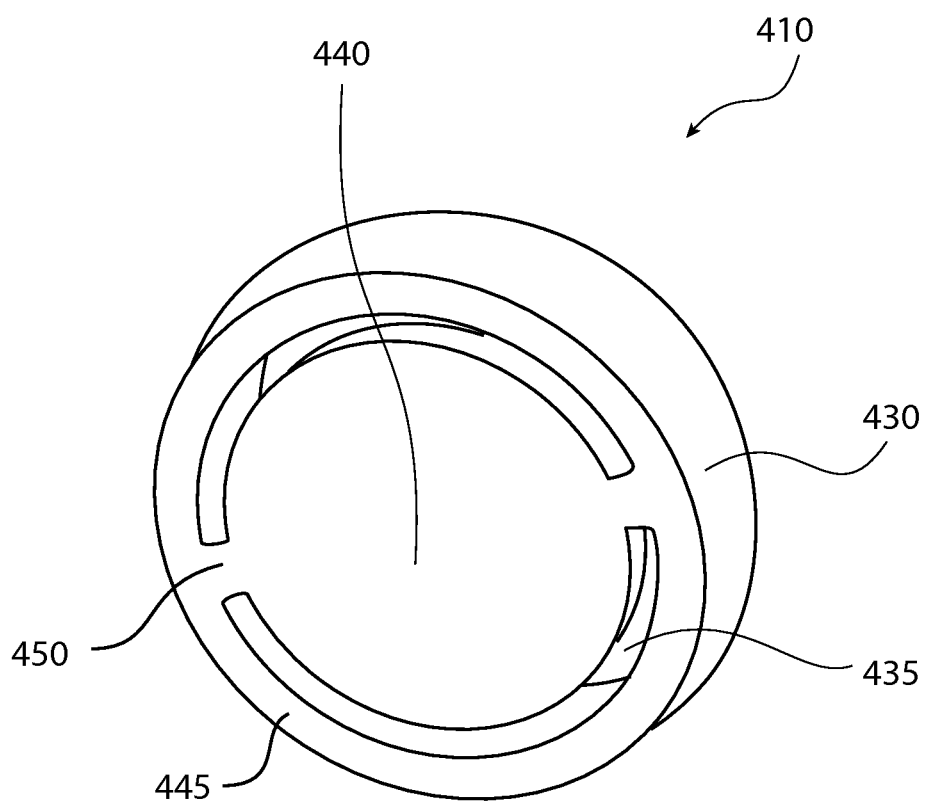
FIG. 4 is a perspective view of a restrictor in accordance with one embodiment presented herein.

FIG. 4 is a front-side perspective view of a restrictor 410, in accordance with another embodiment presented herein. Restrictor 410 includes an outer annular ring 445 and a circular central body, or portion 440. Outer ring 445 and central portion 440 are connected via a plurality of bridge connections 450. Restrictor 410 includes a cylindrical wall 430, which may be flat or tapered. The back side of central portion 440 (not shown) is preferably conical to facilitate the dispensing of analyte test strips 104 through arc-shaped openings 435. Additional tapered or flat surfaces may be provided on the back side of restrictor 410 in order to guide analyte test strips through arc-shaped openings 435. In one embodiment, the width of arc-shaped opening is about 0.045+/−0.005 inches. In one embodiment, restrictor 410 is formed from a hard plastic mold.

Figure 5A:
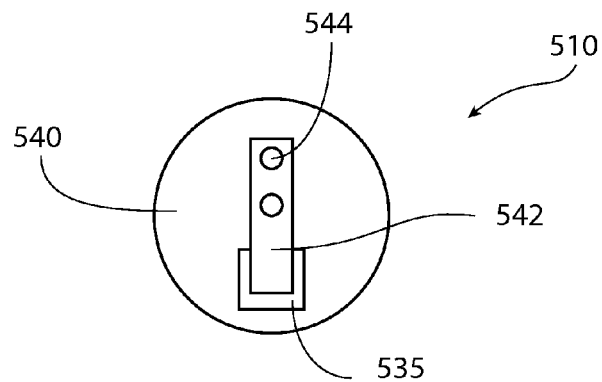
FIG. 5A is a front-side view of a restrictor in accordance with one embodiment presented herein.
Figure 5B:
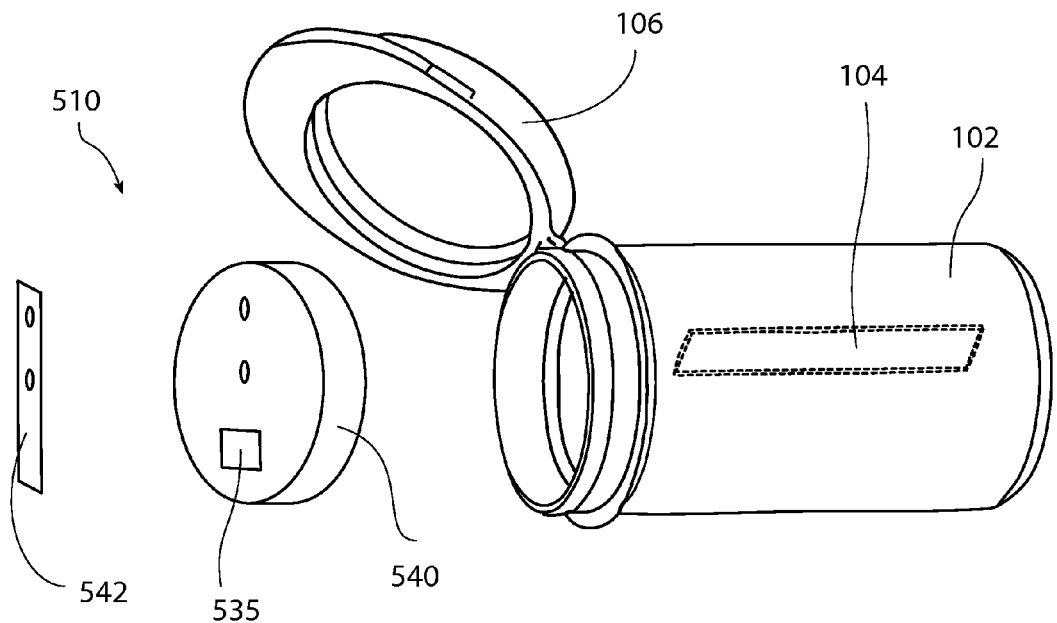
FIG. 5B is an exploded view of the restrictor of FIG. 5A, in combination with an analyte test strip container.
Figure 5C:
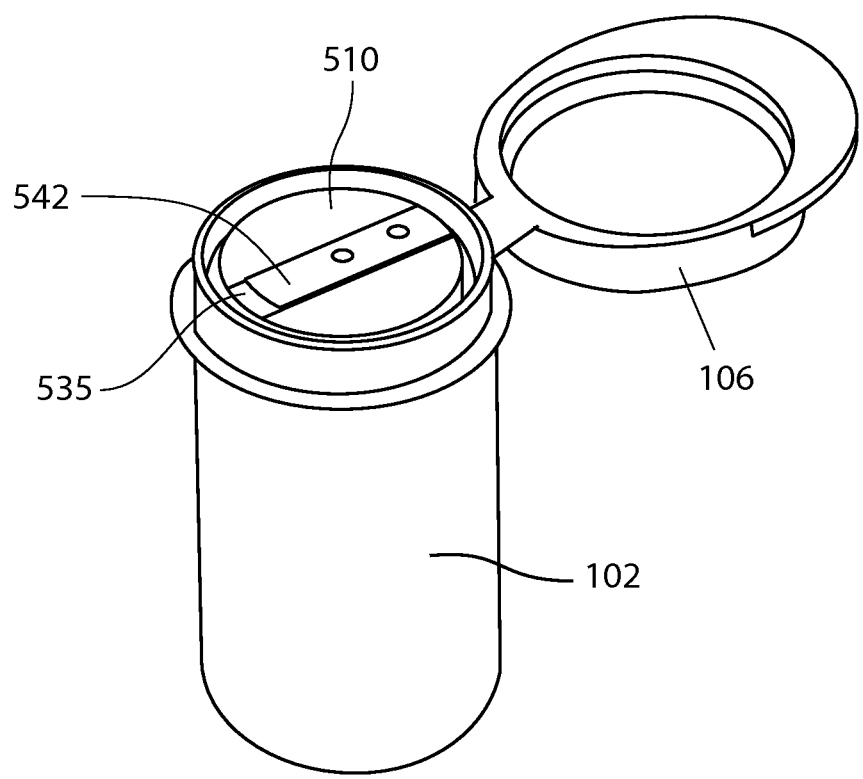
FIG. 5C is a perspective view of the embodiment depicted in FIG. 5B.

FIG. 5A is a front-side view of a restrictor 510, in accordance with one embodiment presented herein. FIG. 5B is an exploded view of restrictor 510, in combination with container 102. FIG. 5C illustrates restrictor 510 inserted within an open end of container 102. Restrictor 510 includes a cylindrical base member 540 and a restrictor plate 542. In one embodiment, plate 542 is attached to base 540 via rivets 544. In alternative embodiments, other attachment means may be incorporated. Plate 542 is sized and positioned to partially cover an opening 535 in base 540. As such, when container 102 is tilted and/or shaken, a controlled number of analyte test strips 104 can be dispensed from container 102. Cap 106 is used to close the open end of container 102.

FIG. 6A is a front-side angled view of a restrictor 610, in accordance with another embodiment of the present invention. FIG. 6B is a front-side view of restrictor 610. FIG. 6C is a back-side angled view of restrictor 610. FIG. 6D is a side view of restrictor 610. Restrictor 610 is formed of a hard plastic mold. Restrictor 610 generally includes an outer annular ring 645 and a circular central body portion 640. As shown, outer ring 645 is a multi-faceted ring with a cylindrical side wall 630 and a tapered inner wall 644. A continuous setting ring 660 is provided around side wall 630. Setting ring 660 aids in the permanent (or semi-permanent) mating (or lodging) of restrictor 610 in container 102. A tapered abutment surface 643 is provided on the lower portion of restrictor 610. When restrictor 610 is inserted into container 102, abutment surface 643 mates against shoulder region 205 within container 102.

Central body portion 640 is concentrically positioned within outer ring 645. Bridge connections 650 are provided as links between central body portion 640 and outer ring 645. The spacing between central body portion 640 and outer ring 645 creates arc-shaped openings (or radial slots) 635. Central body portion 640 is shown as a multi-faceted surface having funneled and/or tapered inner surfaces 642. Central body portion 640 also includes a central opening 636. A plurality of teeth structures 611 are uniformly spaced around the edge of central opening 636. Gaps 612 between each tooth 611 are sized to allow the passage of one or more analyte test strips therethrough.

In operation, tapered inner surfaces 642 and tapered inner wall 644 serve to direct analyte test strips through arc-shaped openings 635 or central opening 636. Inner surfaces 642 and tapered inner wall 644 are also angled appropriately to serve a braking function when an analyte test strip is proceeding through arc-shaped openings 635 or central opening 636. In the event that one or more unwanted analyte test strips are dispensed from the container, arc-shaped openings 635 and/or central opening 636 may be used to return any unwanted test strips to the container. By selection of the appropriate dimensions, arc-shaped openings 635 and central opening 636 are designed to dispense analyte test strips in a controlled manner. Such dimensions are discussed below in more detail with respect to the embodiment shown in FIGS. 7A-7H.

Figure 7A:
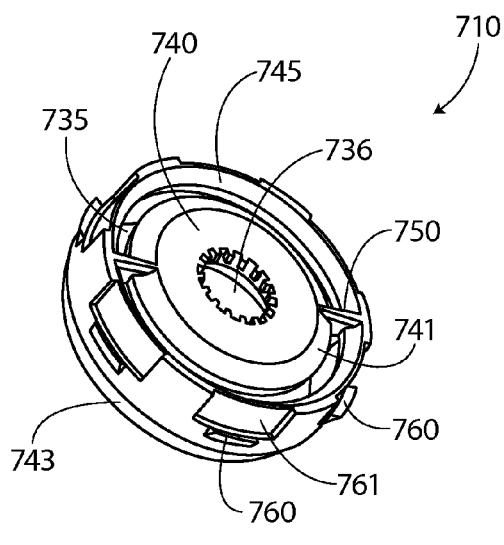
FIG. 7A is a front-side angled view of a restrictor in accordance with another embodiment presented herein.
Figure 7B:
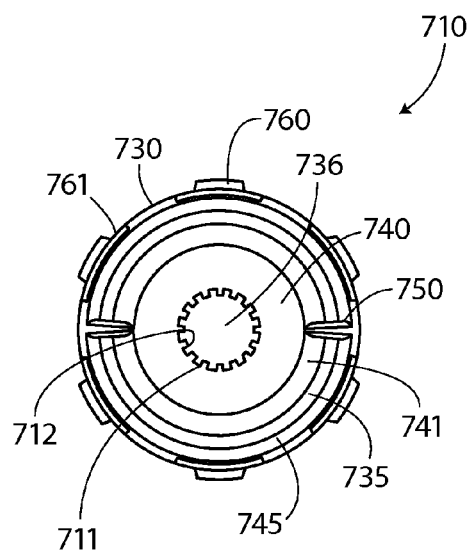
FIG. 7B is a front-side view of the restrictor of FIG. 7A.
Figure 7C:
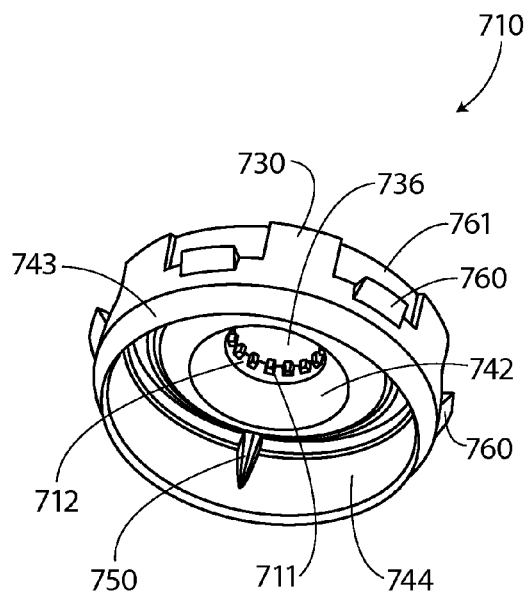
FIG. 7C is a back-side angled view of the restrictor of FIG. 7A.
Figure 7D:
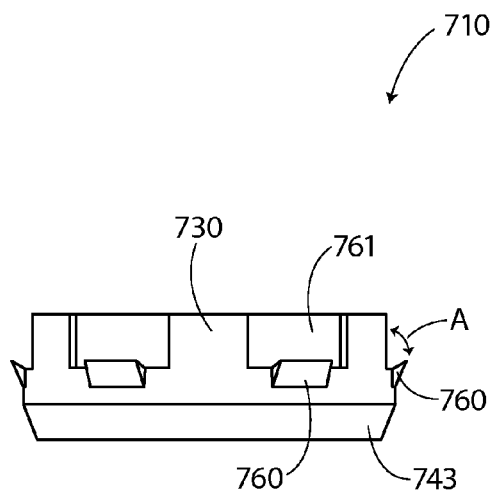
FIG. 7D is a side view of the restrictor of FIG. 7A.
Figure 7E:
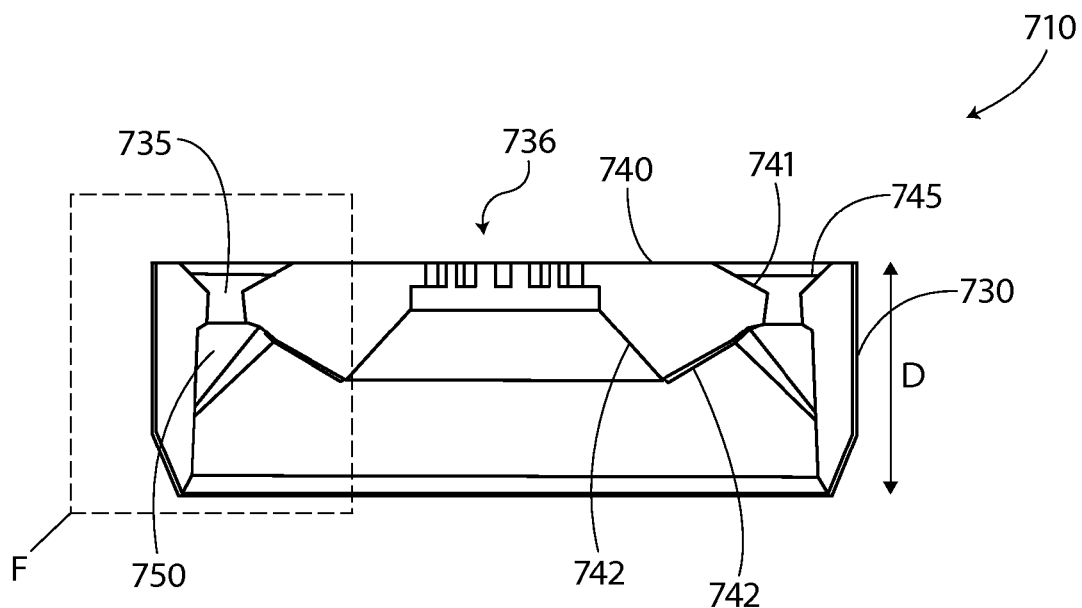
FIG. 7E is a cross-sectional view of the restrictor of FIG. 7A.
Figure 7F:
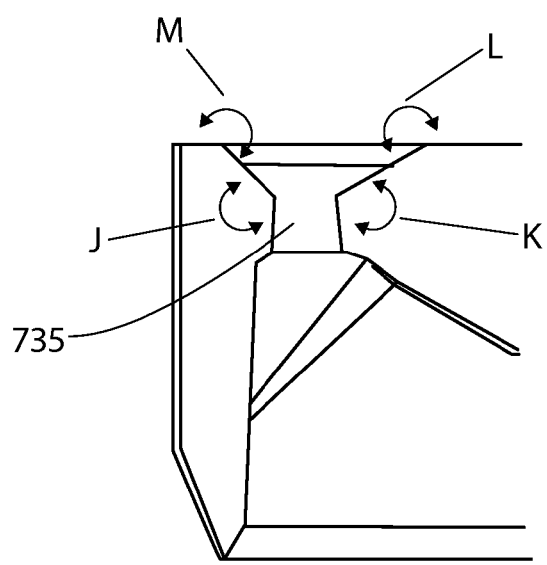
FIG. 7F is a partial sectional view of the restrictor of FIG. 7A.
Figure 7G:
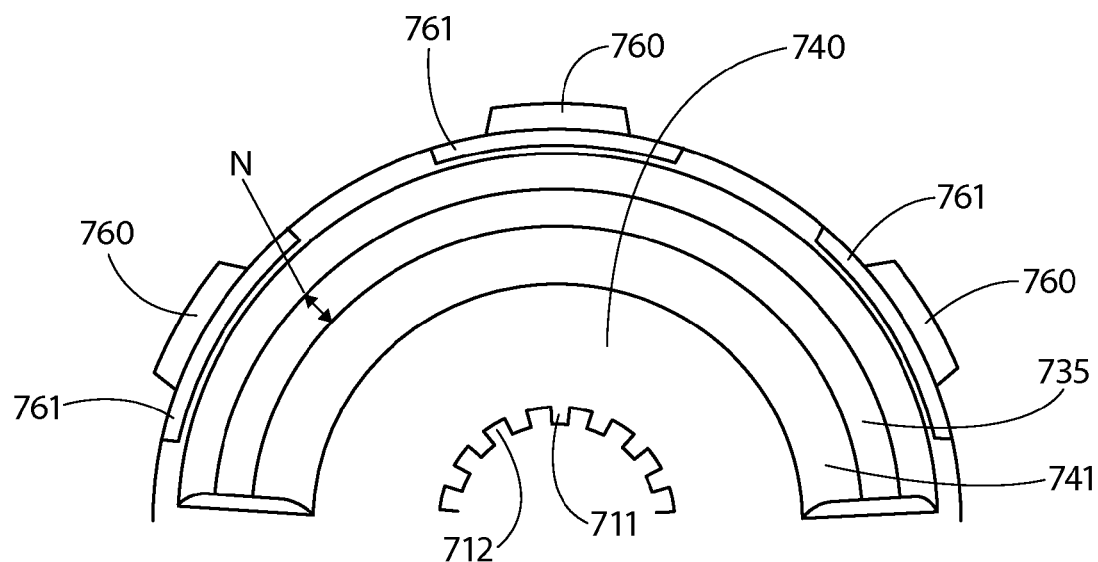
FIG. 7G is a partial sectional view of the restrictor of FIG. 7A.
Figure 7H:
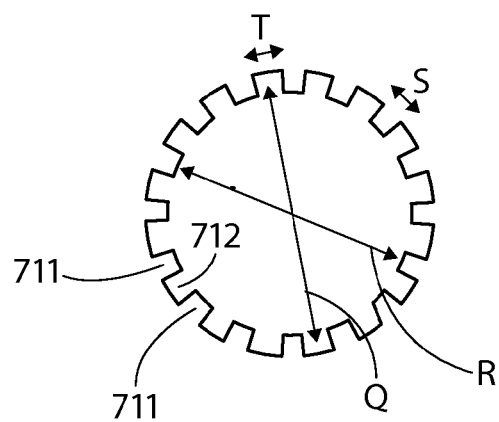
FIG. 7H is a partial sectional view of the restrictor of FIG. 7A.

FIG. 7A-7H present yet another alternative embodiment. FIG. 7A is a front-side angled view of a restrictor 710. FIG. 7B is a front-side view of restrictor 710. FIG. 7C is a back-side angled view of restrictor 710. FIG. 7D is a side view of restrictor 710. FIG. 7E is a cross-sectional view of restrictor 710. FIG. 7F is a partial sectional view of restrictor 710 taken from cut-out "F" of FIG. 7E. FIG. 7G is a partial sectional view of restrictor 710. FIG. 7H is a partial sectional view of restrictor 710.

Restrictor 710 generally includes an outer annular ring 745 and a circular central body portion 740. As shown, outer ring 745 is a multi-faceted ring with a cylindrical side wall 730 and a tapered inner wall 744. A tapered abutment surface 743 is provided on the lower portion of outer ring 745. Abutment surface 743 serves to mate against shoulder region 205 when restrictor 710 is inserted within container 102. Restrictor 710 differs from restrictor 610 in that restrictor 710 includes a non-continuous setting ring formed of a plurality of tabs 760. Tabs 760 are provided around side wall 730 to aid in the permanent (or semi-permanent) mating (or lodging) of restrictor 710 within container 102. Because tabs 760 do not fully encircle side wall 730, restrictor 710 may be more easily removed from within container 102. Further, a plurality of cavities 761 are provided to allow a degree of flex in side wall 730 when restrictor 710 is being removed from within container 102.

In one embodiment, restrictor 710 includes six tabs 760. In alternative embodiments, one or more tabs 760 may be used. Tabs 760 may include an angle of vertical trajectory "A" (offset from side wall 730) of about 60°+/−5°; or alternatively less than 90°. Each tab 760 may have an angular length in relation to the circumference of restrictor 710 of about 20°+/−5°.

Central body portion 740 is concentrically positioned within outer ring 745. Bridge connections 750 are provided as links between central body portion 740 and outer ring 745. The spacing between central body portion 740 and outer ring 745 creates arc-shaped openings (or radial slots) 735. Central body portion 740 is shown as a multi-faceted surface having funneled or tapered inner surfaces 742. Central body portion 740 also includes a central opening 736. A plurality of teeth structures 711 are uniformly spaced around the edge of central opening 736. Gaps 712 between each tooth 711 are sized to allow the passage of one or more analyte test strips therethrough. For example, sixteen uniformly spaced teeth 711 may be provided. The distance "Q" between opposing gaps 712 may be about 0.270+/−0.003 inches; or equal to $$\left(\frac{9}{8}w\right) + /-\left(\frac{1}{64}w\right)$$

where "w" is the width of an analyte test strip. The distance "R" between opposing teeth 711 may be about 0.230+/−0.003 inches; or equal to $$\left(\frac{31}{32}w\right) + /-\left(\frac{1}{64}w\right)$$

where "w" is the width of an analyte test strip. The width "S" of each gap may be about 0.030+0.015/−0.010 inches; or equal to 1.25w+/−0.25w, where "w" is the width of an analyte test strip. The width "T" of each tooth may be about 0.015+/−0.010 inches; or set as a function of the gap width "S" and number of teeth 711.

In operation, tapered inner surfaces 742 and tapered inner wall 744 serve to direct analyte test strips through arc-shaped openings 735 or central opening 736. Inner surfaces 742 and tapered inner wall 744 are also angled appropriately to serve a braking function when an analyte test strip is proceeding through arc-shaped openings 735 or central opening 736. In the event that one or more unwanted analyte test strips are dispensed from the container, arc-shaped openings 735 and/or central opening 736 may be used to return any unwanted test strips to the container.

In one embodiment, restrictor 710 is provided with two arc-shaped openings 735. In alternative embodiment, two or more arc-shaped openings may be employed. Each arc-shaped opening may have a gap width of about 0.045+/−0.005 inches; or a gap width which is a function of the thickness of the analyte test strip, wherein the gap width is equal to 1.9z+/−0.1z, wherein "z" is the thickness of the analyte test strip. Each arc-shaped opening may be about 172°+/−3°; or about 40° to about 175°. Each arc-shaped opening may have an outer radius of about 0.395+/−0.050 inches, and an inner radius of about 0.350+/−0.050 inches, wherein the inner radius is smaller than the outer radius. Alternatively, the inner radius may be determined by the following equation:

$$r = \sqrt{R^2 - \frac{w^2}{4}} - z$$

wherein "r" is the inner radius; "R" is the outer radius; "w" is the width of the analyte test strip; and "z" is the thickness of the analyte test strip. Further, each arc-shaped opening may have an angle of strip entry "J" (outer diameter) of about 130°+/−5°; or 130°+/−30°. Each arc-shaped opening may have an angle of strip entry "K" (inner diameter) of about 112°+/−5°; or a/bout 110°+/−30°. Each arc-shaped opening may have an angle of strip exit "M" (outer diameter) of about 210°+/−5°; or about 210°+/−30°. Each arc-shaped opening may have an angle of strip exit "N" (inner diameter) of about 225°+/−5°; or about 225°+/−30°.

In one embodiment, restrictor 710 includes a diameter of about 0.930+/−0.005 inches and a diameter with tabs 760 of about 0.980+/−0.005 inches. In one embodiment, restrictor 710 has a thickness "D" of about 0.300+/−0.050 inches. The dimensions provided with respect to the embodiment shown in FIGS. 7A-7H are applicable, where appropriate, to any and all embodiments provided herein.

FIG. 8A is a front-side angled view of a symmetrical restrictor 810, in accordance with one embodiment presented herein. FIG. 8B is a front-side view of restrictor 810. FIG. 8C is a side view of restrictor 810. Restrictor 810 generally includes an outer annular ring 845 and a circular central body portion 840 recessed within outer ring 845. As shown, outer ring 845 is a multi-faceted ring with a symmetrical side wall 830a, 830b and a tapered inner wall. Outer ring 845 also includes abutment surfaces 843a, 843b to mate against shoulder region 205 when restrictor 810 is inserted within container 102. The symmetry of restrictor 810 allows for the restrictor to be inserted into a container in either direction.

Central body portion 840 is concentrically positioned within outer ring 845. Bridge connections 850 are provided as links between central body portion 840 and outer ring 845. The spacing between central body portion 840 and outer ring 845 creates arc-shaped openings (or radial slots) 835. Central body portion 840 is shown as a multi-faceted surface having funneled or tapered surfaces. Central body portion 840 also includes a central opening 836. A plurality of teeth structures 811 are uniformly spaced around the edge of central opening 836. Gaps between each tooth 811 are sized to allow the passage of one or more analyte test strips therethrough.

In operation, tapered surfaces of central portion 840 and tapered inner walls of outer ring 845 serve to direct analyte test strips through arc-shaped openings 835 or central opening 836. The dimensions of arc-shaped openings 835 and central opening 836 are selected such that analyte test strips are dispensed in a controlled manner. Such dimensions are discussed above with respect to the embodiment shown in FIGS. 7A-7H.

FIG. 9A is a front-side angled view of a restrictor 910, in accordance with one embodiment presented herein. FIG. 9B is a front-side view of restrictor 910. FIG. 9C is a side view of restrictor 910. Restrictor 910 is similar to restrictor 710, discussed above. Restrictor 910, however, provides symmetrical tabs 960 and cavities 961 such that the restrictor 910 may be inserted into a container in either direction. Like restrictor 710, restrictor 910 generally includes a tapered outer annular ring 945 and a circular central body portion 940. The sizing of arc-shaped openings 935 and central opening 936 is designed to dispense analyte test strips in a controlled manner. Such dimensions are discussed above with respect to the embodiment shown in FIGS. 7A-7H.

Figure 10:
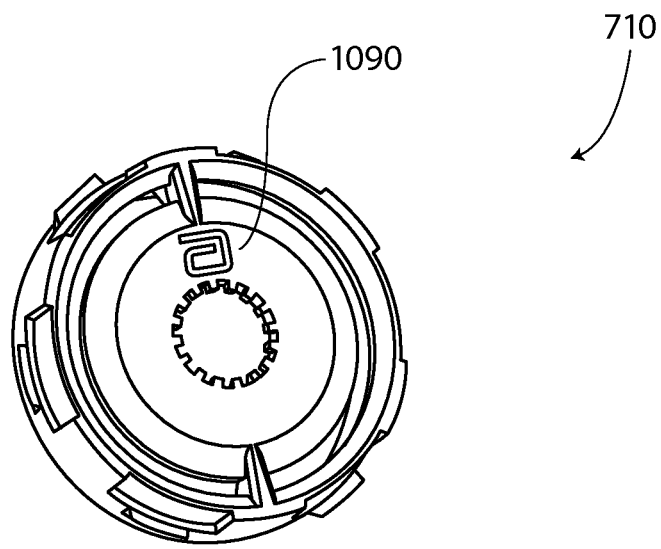
FIG. 10 is a front-side angled view of a restrictor in accordance with an embodiment presented herein.
Figure 11:
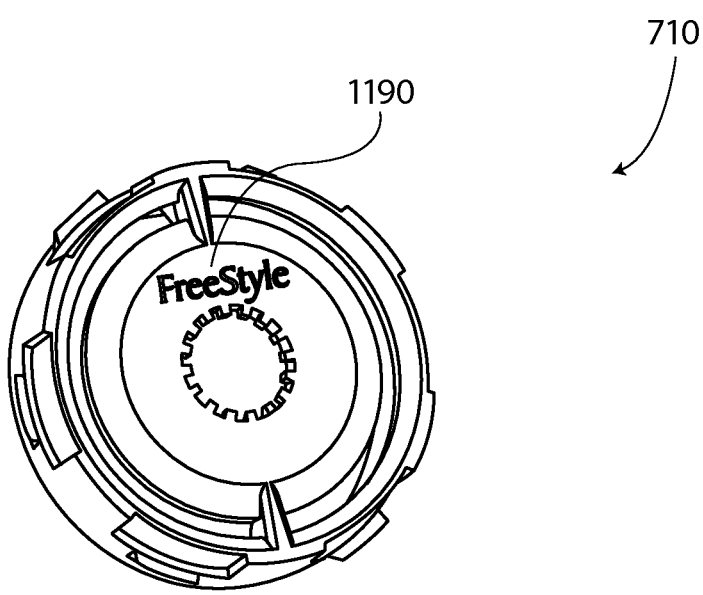
FIG. 11 is a front-side angled view of a restrictor in accordance with an embodiment presented herein.
Figure 12:
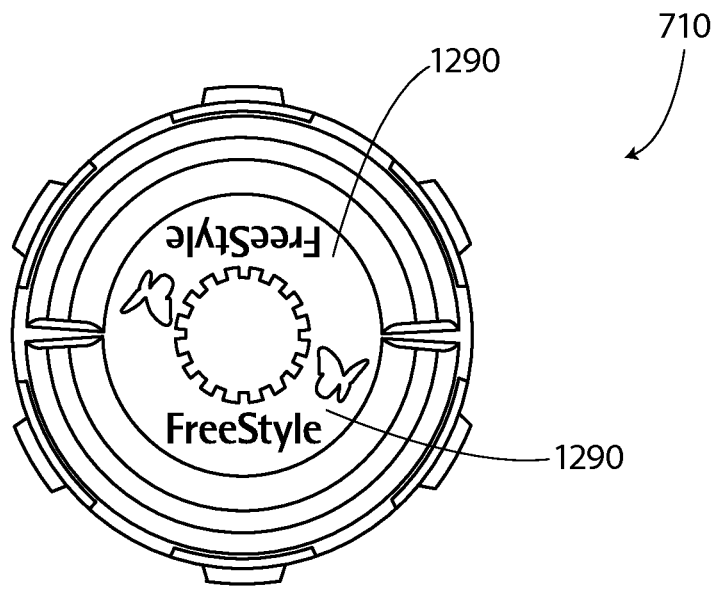
FIG. 12 is a front-side angled view of a restrictor in accordance with yet an embodiment presented herein.
Figure 13:
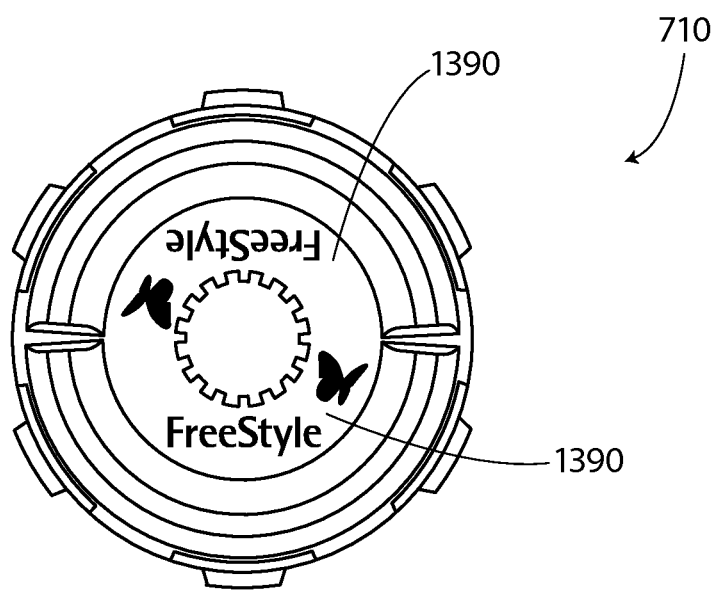
FIG. 13 is a front-side angled view of a restrictor in accordance with an embodiment presented herein.
Figure 14:
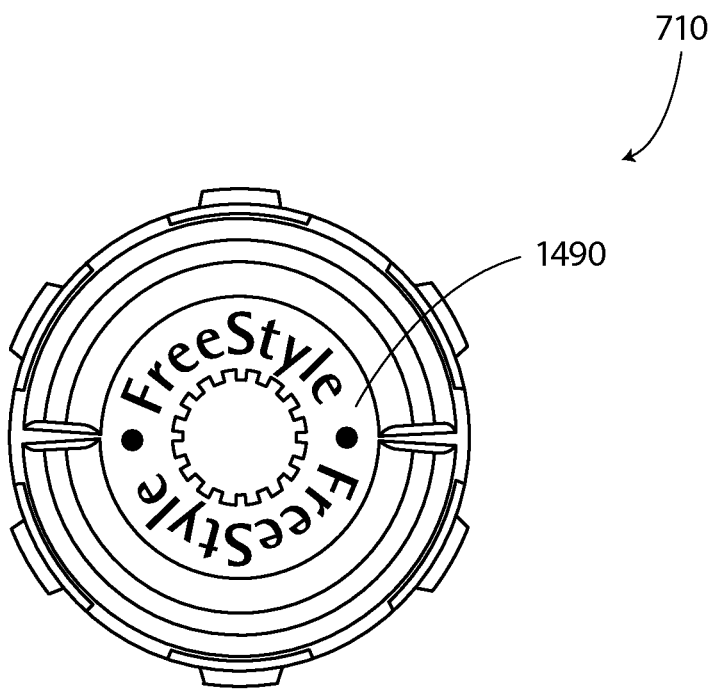
FIG. 14 is a front-side angled view of a restrictor in accordance with an embodiment presented herein.

FIG. 10 is a front-side angled view of restrictor 710 displaying a logo in area 1090. FIG. 11 is a front-side angled view of restrictor 710 displaying a logo in area 1190. FIG. 12 is a front-side angled view of restrictor 710 displaying a logo in area 1290. FIG. 13 is a front-side angled view of restrictor 710 displaying a logo in area 1390. FIG. 14 is a front-side angled view of restrictor 710 displaying a logo in area 1490.

EXAMPLES

The following paragraphs serve as further example embodiments of the above-described systems. The examples provided are prophetic examples, unless explicitly stated otherwise.

Example 1

In one embodiment, the present disclosure provides a dispenser insert for a storage vial configured to hold analyte sensors. The dispenser insert includes an opening configured to allow a user to dispense a single analyte sensor at a time.

The dispenser insert functions as a restrictor restricting the number of analyte sensors dispensed at one time. A user may dispense a single analyte sensor from a vial which includes the dispenser insert by tilting the vial, shaking the vial, and dispensing and/or withdrawing a single analyte sensor which protrudes through the opening in the dispenser insert.

In one embodiment, the opening in the dispenser insert includes a serrated or "saw tooth" edge which facilitates the dispensing of a single analyte sensor at a time. Other edge patterns may be utilized to limit the possibility of simultaneously dispensing multiple analyte sensors. The dispenser insert may be configured to be inserted into and operate with a pre-existing storage vial, which includes a storage portion and an integrated vial cap.

The dispenser insert may help prevent unintended spillage and potential contamination of analyte sensors which may result when a user attempts to dispense an analyte sensor from a storage vial.

Example 2

In one embodiment, there is provided a dispenser insert, which includes multiple exit ports that are positioned near the inside wall of a storage vial when the dispenser is positioned in the storage vial. This configuration serves to promote the exit of individual or small numbers of analyte sensors in a manageable way. In one embodiment, the exits ports are in the form of perimeter slits which follow the curve of the vial wall. The dispenser insert is configured such that the cap of the storage vial can be closed over the dispenser insert positioned in the storage vial to form a seal. By shaking the storage vial with the opening side pointed downward, velocity and gravity propel and translate the stored analyte sensors toward and out of the exit(s). In some embodiments, the shape of the dispenser insert causes friction on the faces of the analyte sensors creating drag which brakes their movement. During this process, one strip generally falls from the port at a time. The action of dispensing a single analyte sensor at a time may be facilitated by the width of the port which may be configured such that the port does not allow more than one thickness of analyte sensor to pass through it. In another embodiment, a user may shake the vial including the dispenser insert until one or more analyte sensors extend far enough that one can be grasped with two fingers and extracted. The others may be returned to the storage portion of the vial by turning the vial upright.

Example 3

In another embodiment, there is provided a dispenser insert which includes a center hole which facilitates strip exit when the vial is approximately half full, e.g., about 25 analyte sensors where the vial generally includes about 50 analyte sensors. Inclusion of this center hole may decrease the number of shakes required to obtain an analyte sensor from the vial. The center hole may be configured to include "teeth" or stops to promote exit of only one strip at a time. These teeth or stops are positioned around the edge of the center hole and extend towards the center of the circle. The teeth or stops may be positioned such that the openings between the teeth are less than two times the thickness of an individual analyte sensor. This helps to prevent or decrease the likelihood that two analyte sensors that are in face to face contact will exit at the same time. The exiting analyte sensor itself also helps to prevent or decrease the likelihood that analyte sensors that are oriented at angles to the exiting analyte sensor will use the center exit port at the same time.

Example 4

In another embodiment, there is provided a dispenser insert that includes a handle in the center instead of a hole. This handle can be used to facilitate removal of the dispensing insert in the case where the user does not want to use it.

Example 5

In one embodiment, the dispenser insert is configured for non-symmetrical insertion into the analyte sensor storage vial. In other words, the dispenser insert is designed to be inserted in only one orientation and cannot be inserted in the opposite upside down orientation. In other embodiments, the dispenser insert is configured for symmetrical insertion and may be inserted into the storage vial in either a right side up or upside down orientation.

While the dispenser inserts of the present disclosure may include more than two exit ports that are positioned near the inside wall of the storage vial when inserted, in some embodiments the dispenser inserts include exactly two such ports in the form of slits which extend nearly half way around the dispenser insert with a small bridge section of material in between them. This configuration not only minimizes barriers to analyte sensor emigration but also enables removal of the center of the dispenser insert to accommodate the needs of those users who do not want to use the dispenser insert. The center section can be removed by pressing on one side, 90 degrees to the bridge sections. This will cause the center section to rotate. If the center section is rotated far enough, it will break off at the bridge sections and can be discarded leaving a large hole for extracting analyte sensors which hole is similar in size to opening in the vial without the dispenser inserted.

The dispenser inserts of the present disclosure may be fabricated as one piece with a multi-cavity injection mold using any suitable material, e.g., a suitable polymer material. The dispenser inserts may be inserted into the analyte sensor storage vials on the packaging line or can be included in a box of analyte sensor storage vials so that a user can make a choice as to whether to use the dispenser inserts or not.

Example 6

In one embodiment, there is provided a dispenser insert that includes an exit port positioned near the side, inside wall, or rim of an analyte sensor storage vial in which the dispenser insert is configured to be inserted and a covering flap to restrict analyte sensor outflow. The covering flap may be configured to engage features of the dispenser insert, e.g., using a snap-fit engagement mechanism. The dispenser insert is sized and shaped to be inserted into the interior of the storage vial and once inserted allows for closure and seal of the vial using an integrated vial cap. When the storage vial is held upside down with the opening on the bottom, gravity accumulates the analyte sensors near the exit. The flap functions as a restrictor which drags on the exiting analyte sensors and brakes their uncontrolled motion. In this way, one or more analyte sensors are arrested in a position, part way inside and part way outside, so that one can be separated and removed and the others returned to the vial by simply turning it upright. This configuration may be used with the flap or without the flap and the flap may be removed by simply pulling it off. Without the flap, the user can hold their fingers in front of the exit and allow a few analyte sensors to partially exit, then separate one and let the others slide back into the product container.

The dispenser insert-flap combination may be fabricated as two separate pieces. Alternatively, the dispenser insert-flap combination may be injected molded as a single component.

For a variety of reasons it may be desirable, when using a dispenser insert as described herein, to preserve the storage vial's ability to form a proper seal with the storage vial cap. For example, the storage vial and cap may include specific features that prevent analyte sensor degradation due to moisture. Accordingly, in some embodiments the dispenser inserts described herein are specifically configured such that upon insertion into a corresponding storage vial, the normal operation of the storage vial and cap is not affected. This may be accomplished by configuring the dispenser inserts to be inserted either flush with the opening or recessed below the opening of the storage vial. The dispenser inserts may also be configured to include a ring or hoop structure that protrudes from the outside diameter of the dispenser insert. The dispenser inserts may be configured such that the position of this ring or hoop is as deep as possible when inserted so as to minimize interference with the fit of the vial cap with the vial. This configuration is such that the user may install or remove the dispenser insert if needed. Additionally, this configuration is such that the dispenser insert may be installed either manually or in an automatic fashion during the packaging of the analyte sensor storage vials.

Although the dispenser inserts described herein have been discussed in the context of storage vials designed to hold analyte sensors, it should be noted that storage vials utilizing the disclosed dispenser inserts may be utilized in other contexts. For example, the disclosed dispenser inserts may be utilized in connection with the metering and/or dispensing of discrete goods such as pharmaceutical tablets from a bottle.

CONCLUSION

The foregoing description of the invention has been presented for purposes of illustration and description. It is not intended to be exhaustive or to limit the invention to the precise form disclosed. Other modifications and variations may be possible in light of the above teachings. The embodiments were chosen and described in order to best explain the principles of the invention and its practical application, and to thereby enable others skilled in the art to best utilize the invention in various embodiments and various modifications as are suited to the particular use contemplated. It is intended that the appended claims be construed to include other alternative embodiments of the invention; including equivalent structures, components, methods, and means.

It is to be appreciated that the Detailed Description section, and not the Summary and Abstract sections, is intended to be used to interpret the claims. The Summary and Abstract sections may set forth one or more, but not all exemplary embodiments of the present invention as contemplated by the inventor(s), and thus, are not intended to limit the present invention and the appended claims in any way.

What is claimed is:

1. A vial adapted for dispensing analyte test strips in a controlled manner, comprising:
    a cylindrical container for holding a plurality of analyte test strips, the container having a base, a cylindrical wall with an interior surface, an interior shoulder along the interior surface, and an open end;
    a cap coupled to the container for closing the open end of the container; and
    an insert sized to fit within the open end of the container and mate with the interior shoulder of the container, wherein the insert includes an outer ring, a circular interior body portion concentrically aligned within the outer ring and spaced from the outer ring, and a plurality of bridge structures linking the outer ring to the interior body portion so as to create a plurality of arc-shaped openings between the outer ring and the interior body portion, wherein the plurality of arc-shaped opening extend through the insert into the cylindrical container.

2. The vial of claim 1, wherein the outer ring includes a tapered surface to mate with the interior shoulder of the container.

3. The vial of claim 1, wherein the outer ring, plurality of bridge structures, and interior body portion are aligned flush with one another.

4. The vial of claim 1, wherein each arc-shaped openings have a width between about 0.030 inches and about 0.060 inches.

5. The vial of claim 1, wherein the interior body portion includes a flat surface on plane with a surface of the outer ring, and a conical opposing surface.

6. The vial of claim 1, wherein the interior body portion is recessed within the outer ring.

7. The vial of claim 1, wherein the interior body portion has a multifaceted surface.

8. The vial of claim 1, wherein the bridge structures are tapered.

9. The vial of claim 1, further comprising a desiccant bound to the interior surface of the container.

10. The vial of claim 1, wherein the insert includes a central opening in the interior body portion.

11. The vial of claim 10, wherein the central opening is generally circular.

12. The vial of claim 11, wherein the central opening has a diameter between about 0.20 inches and about 0.35 inches.

13. The vial of claim 11, wherein an edge of the interior body portion about the central opening includes a plurality of teeth structures.

14. The vial of claim 13, wherein the plurality of teeth structures are uniformly spaced around the edge of the interior body about the central opening.

15. The vial of claim 13, wherein each of the plurality of teeth structures is spaced between about 0.015 inches and about 0.050 inches from an adjacent one of the plurality of teeth structures.

16. The vial of claim 13, wherein opposing teeth structures are distanced between about 0.20 inches and about 0.30 inches from one another.

17. The vial of claim 13, wherein each of the plurality of teeth structures is tapered.

18. The vial of claim 1, wherein the insert is non-removable once positioned in the vial.

19. The vial of claim 1, wherein the insert is removable once positioned in the vial.

20. A vial adapted for dispensing analyte test strips in a controlled manner, comprising:
    a cylindrical container for holding a plurality of analyte test strips, the container having a base, a cylindrical wall with an interior surface, an interior shoulder along the interior surface, a desiccant bound to the interior surface of the container, and an open end;
    a cap hinged to the container for closing the open end of the container with a snap-fit engagement; and
    a cylindrical insert sized to fit within the open end of the container and mate with the interior shoulder of the container, wherein the insert includes an annular outer ring, wherein the annular outer ring includes tapered edges, a plurality of uniformly spaced cavities on an exterior surface of the annular outer ring, and a plurality of uniformly spaced tabs extending from the exterior surface of the annular outer ring, a multifaceted, circular interior body concentrically aligned within the annular outer ring, wherein the circular interior body includes a generally circular central opening having a plurality of uniformly spaced teeth structures about an edge of the central opening, wherein each of the plurality of teeth structures is spaced between about 0.020 inches and about 0.045 inches from an adjacent one of the plurality of teeth structures, and wherein opposing teeth structures are distanced between about 0.227 inches and about 0.273 inches from one another, and a plurality of bridge structures linking the annular outer ring to the circular interior body so as to create a plurality of arc-shaped exit ports.

21. The vial of claim 20, wherein the insert is non-removable once positioned in the vial.

22. The vial of claim 20, wherein the insert is removable once positioned in the vial.

23. An insert for an analyte test strip vial, comprising:

an annular outer ring, wherein the annular outer ring includes tapered edges, a plurality of uniformly spaced cavities on an exterior surface of the annular outer ring, and a plurality of uniformly spaced tabs extending from the exterior surface of the annular outer ring;

a multifaceted, circular interior body concentrically aligned within the annular outer ring, wherein the circular interior body includes a generally circular central opening having a plurality of uniformly spaced teeth structures about an edge of the central opening, wherein each of the plurality of teeth structures is spaced between about 0.020 inches and about 0.045 inches from an adjacent one of the plurality of teeth structures, and wherein opposing teeth structures are distanced between about 0.227 inches and about 0.273 inches from one another; and a plurality of bridge structures linking the annular outer ring to the circular interior body so as to create a plurality of arc-shaped exit ports.

24. An insert for an analyte test strip vial, comprising:

an annular outer ring, wherein the annular outer ring includes tapered edges, a plurality of uniformly spaced cavities on an exterior surface of the annular outer ring, and a plurality of uniformly spaced tabs extending from the exterior surface of the annular outer ring;

a multifaceted, circular interior body concentrically aligned within the annular outer ring and spaced from the outer ring, wherein the circular interior body includes a generally circular central opening having a plurality of uniformly spaced teeth structures about an edge of the central opening; and a plurality of bridge structures linking the annular outer ring to the circular interior body so as to create a plurality of arc-shaped exit ports.

* * * * *